(12) United States Patent
Gopichandran et al.

(10) Patent No.: US 10,159,712 B2
(45) Date of Patent: Dec. 25, 2018

(54) EMBRYO IMPLANTATION

(71) Applicant: Ostara Biomedical Ltd, Liverpool, Merseyside (GB)

(72) Inventors: Nadia Gopichandran, Liverpool (GB); Nicolas Michel Orsi, Liverpool (GB); David Andrew Brooke, Liverpool (GB)

(73) Assignee: Ostara Biomedical Ltd. (GB)

( * ) Notice: Subject to any disclaimer, the term of this patent is extended or adjusted under 35 U.S.C. 154(b) by 293 days.

(21) Appl. No.: 14/457,360

(22) Filed: Aug. 12, 2014

(65) Prior Publication Data
US 2015/0051441 A1 Feb. 19, 2015

Related U.S. Application Data

(60) Provisional application No. 61/868,764, filed on Aug. 22, 2013.

(30) Foreign Application Priority Data

Aug. 13, 2013 (GB) .................................. 1314452.2

(51) Int. Cl.
*A61K 38/21* (2006.01)
*A61D 19/02* (2006.01)
(Continued)

(52) U.S. Cl.
CPC .............. *A61K 38/217* (2013.01); *A61D 19/00* (2013.01); *A61D 19/02* (2013.01); *A61D 19/04* (2013.01);
(Continued)

(58) Field of Classification Search
CPC .............. A61K 38/195; A61K 38/2006; A61K 38/191; A61K 38/1841; A61K 9/0036;
(Continued)

(56) References Cited

U.S. PATENT DOCUMENTS 6,258,998 B1 * 7/2001 Damiani .............. C12N 5/0606
800/17
7,204,978 B1 * 4/2007 Robertson .............. A61K 35/19
424/184.1
(Continued)

FOREIGN PATENT DOCUMENTS

GB 1 393 628 5/1975
GB 2 003 386 A 3/1979
(Continued)

OTHER PUBLICATIONS

Bathini et al. "2-Aminoquinazoline inhibitors of cyclin-dependent kinases", *Bioorganic & Medicinal Chemistry Letters* 15:3881-3885 (2005).
(Continued)

*Primary Examiner* — Navin Natnithithadha
*Assistant Examiner* — Sunita Reddy
(74) *Attorney, Agent, or Firm* — Ward & Smith, P.A.

(57) ABSTRACT

The present invention relates to methods of and compositions comprising cytokines for, improving the success rate of embryo implantation and the success rate of pregnancy rates in females, by providing an immunopermissive uterine environment prior to insemination or implantation of embryos. The methods of the present invention are used to make the uterus more receptive or less hostile to, for example, transferred embryos, sperm or other allografted tissue.

17 Claims, 3 Drawing Sheets

(51) Int. Cl.
*A61K 9/00* (2006.01)
*A61K 38/19* (2006.01)
*A61D 19/00* (2006.01)
*A61D 19/04* (2006.01)
*A61K 38/18* (2006.01)
*A61K 38/20* (2006.01)

(52) U.S. Cl.
CPC .......... *A61K 9/0034* (2013.01); *A61K 9/0036* (2013.01); *A61K 38/1841* (2013.01); *A61K 38/19* (2013.01); *A61K 38/191* (2013.01); *A61K 38/193* (2013.01); *A61K 38/195* (2013.01); *A61K 38/204* (2013.01); *A61K 38/2006* (2013.01); *A61K 38/206* (2013.01); *A61K 38/208* (2013.01); *A61K 38/2066* (2013.01); *A61K 38/2086* (2013.01)

(58) Field of Classification Search
CPC .. A61K 38/2086; A61K 38/19; A61K 38/217; A61K 38/208; A61K 38/2066; A61K 38/206; A61K 38/204; A61K 38/193; A61D 19/04; A61D 19/02; A61D 19/00
USPC ............. 600/33–35; 424/85.1, 85.2; 514/8.9; 530/351, 399
See application file for complete search history.

(56) References Cited

U.S. PATENT DOCUMENTS

| | | | |
|---|---|---|---|
| 2005/0148023 A1* | 7/2005 | Thadhani | G01N 33/689 435/7.1 |
| 2005/0272636 A1* | 12/2005 | Robertson | A61K 38/08 424/133.1 |
| 2006/0002937 A1* | 1/2006 | Schwaeble | A01K 67/0276 424/146.1 |
| 2006/0008532 A1* | 1/2006 | Govardhan | A61K 9/0019 424/489 |
| 2006/0177459 A1 | 8/2006 | Robertson et al. | |
| 2007/0178605 A1 | 8/2007 | Mor et al. | |
| 2008/0233113 A1* | 9/2008 | Bansal | C07K 16/18 514/1.1 |
| 2010/0093557 A1* | 4/2010 | Kumble | G01N 33/54306 506/9 |
| 2011/0212975 A1 | 9/2011 | Kao et al. | |
| 2012/0115226 A1* | 5/2012 | Stachelsheid | C12M 25/10 435/366 |
| 2016/0213749 A1 | 7/2016 | Gopichandran et al. | |
| 2017/0095536 A1 | 4/2017 | Orsi et al. | |

FOREIGN PATENT DOCUMENTS

| | | |
|---|---|---|
| GB | 2521709 A1 | 7/2015 |
| JP | 2009051827 A | 3/2009 |
| WO | WO 96/21427 | 7/1996 |
| WO | WO 98/39021 A1 | 9/1998 |
| WO | WO 00/25780 A1 | 5/2000 |
| WO | WO 00/68203 A1 | 11/2000 |
| WO | WO 01/19788 A2 | 3/2001 |
| WO | WO 01/64642 A2 | 9/2001 |
| WO | WO 01/64643 A2 | 9/2001 |
| WO | WO 02/00647 A1 | 1/2002 |
| WO | WO 03/007955 A2 | 1/2003 |
| WO | WO 03/064619 A2 | 8/2003 |
| WO | WO 2004/007472 A1 | 1/2004 |
| WO | WO 2004/026333 A1 | 4/2004 |
| WO | WO 2004/085385 A2 | 10/2004 |
| WO | WO 2005/017192 A3 | 2/2005 |
| WO | WO 2005/035717 A3 | 4/2005 |
| WO | WO 2005/115456 A2 | 12/2005 |
| WO | WO 2006/001463 A1 | 1/2006 |
| WO | WO 2007/011759 A2 | 1/2007 |
| WO | WO 2007/088996 A1 | 8/2007 |
| WO | WO 2007/088999 A1 | 8/2007 |
| WO | WO 2007/092353 A3 | 8/2007 |
| WO | WO 2007/113682 A3 | 10/2007 |
| WO | WO 2008/070902 A1 | 6/2008 |
| WO | WO 2008/073670 A2 | 6/2008 |
| WO | WO 2009/010455 A2 | 1/2009 |
| WO | WO 2009/010871 A2 | 1/2009 |
| WO | WO 2009/026717 A1 | 3/2009 |
| WO | WO 2009/076618 A2 | 6/2009 |
| WO | WO 2009/125219 A3 | 10/2009 |
| WO | WO 2009/139784 A1 | 11/2009 |
| WO | WO 2010/048149 A2 | 4/2010 |
| WO | WO 2010/080537 A1 | 7/2010 |
| WO | WO 2010/126528 A1 | 11/2010 |
| WO | WO 2010/126553 A1 | 11/2010 |
| WO | WO 2011/015037 A1 | 2/2011 |
| WO | WO 2011/143752 A1 | 11/2011 |
| WO | WO 2011/159297 A1 | 12/2011 |
| WO | WO 2012/079032 A2 | 6/2012 |
| WO | WO 2012/080729 A2 | 6/2012 |
| WO | WO 2012/123745 A1 | 9/2012 |
| WO | WO 2013/093878 A1 | 6/2013 |
| WO | WO 2014/087218 A1 | 6/2014 |
| WO | WO 2015/022509 A1 | 2/2015 |
| WO | WO 2015/081157 A1 | 6/2015 |

OTHER PUBLICATIONS

Caballero et al. "2D Autocorrelation, CoMFA, and CoMSIA modeling of protein tyrosine kinases' inhibition by substituted pyrido[2,3-d]pyrimidine derivatives", *Bioorganic & Medicinal Chemistry Letters* 16:810-821 (2008).

Search Report under Section 17(5) corresponding to British Application No. GB1314452.2 dated Jan. 7, 2014.

Search Report under Section 17(6) corresponding to British Application No. GB1314452.2 dated May 22, 2014.

Second Search Report under Section 17(6) corresponding to British Application No. GB1314452.2 dated May 22, 2014.

Third Search Report under Section 17(6) corresponding to British Application No. GB1314452.2 dated May 22, 2014.

Search Report under Section 17(5) corresponding to British Application No. GB1414258.2 dated Apr. 28, 2015.

Feinberg et al. "Transforming Growth Factor—β Stimulates Trophoblast Oncofetal Fibronectin Synthesis in Vitro: Implications for Trophoblast Implantation in Vivo", *J. Clinical Endocrinology and Metabolism* 78(5):1241-1248 (1994).

Notification of Transmittal of the International Search Report and the Written Opinion of the International Searching Authority, or the Declaration corresponding to International Application No. PCT/GB2014/052450 dated Oct. 27, 2014.

Chaouat et al, "Immunoendocrine Networks in Pregnancy and Parturition," Regional Immunology, 1994, vol. 6, pp. 295-301.

De et al., "Expression of interleukin 1, interleukin 6 and tumour necrosis factor α in mouse uterus during the peri-implantation period of pregnancy," Journal of Reproduction and Fertility, Ltd., 1993, vol. 97, Issue 1, pp. 83-89.

Gopichandran et al., "Multiplex determination of murine seminal fluid cytokine," Society for Reproduction and Fertility, Reproduction, 2006, vol. 131, pp. 613-621.

Hansen et al., "Mastitis and Fertility in Cattle—Possible Involvement of Inflammation of Immune Activation in Embryonic Mortality," American Journal of Reproductive Immunology, 2004, vol. 51, pp. 294-301.

Kraus et al., "Peripheral Blood Cytokine Profiling During Pregnancy and Post-partum Periods," American Journal of Reproductive Immunology, 2010, vol. 64, Issue 6, pp. 411-426.

Mas et al., "Immune Regulation at the Interface During Early Steps of Murine Implantation: Involvement of Two New Cytokines of the IL-12 Family (IL-23 and IL-27) and of TWEAK," American Journal of Reproductive Immunology, 2003, vol. 59, Issue 4, pp. 323-338.

Orsi et al., "Cytokine Networks and the Regulation of Uterine Function in Pregnancy and Parturition," Journal of Neuroendocrinology, 2008, vol. 20, pp. 462-469.

(56) References Cited

OTHER PUBLICATIONS

Ota et al., "Expression of a2 Vacuolar ATPase in Spermatozoa is Associated with Semen Quality and Chemokine-Cytokine Profiles in Infertile Men," PLoS ONE, Jul. 2013, vol. 8, Issue 7, pp. 1-7.
Shuya et al, "Leukemia Inhibitory Factor Enhances Endometrial Stromal Cell Decidualization in Humans and Mice," PLoS ONE, Sep. 2011, vol. 6, Issue 9, pp. 1-11.
Svensson et al., "Macrophages at the Fetal-Maternal Interface Express Markers of Alternative Activation and Are Induced by M-CSF and IL-10," The Journal of Immunology, 2011, vol. 187, pp. 3617-3682.
Torchinsky et al., "TNF-α acts to prevent occurrence of malformed fetuses in diabetic mice," Diabetologia, 2004, vol. 47. pp. 132-139.
Zollner et al., "LIF and TNF alpha concentrations in embryo culture media are predictive for embryo implantation in IVF," Asian Pacific Journal of Reproduction, 2012, vol. 1, No. 4, pp. 277-282.
Bromfield, "Seminal fluid and reproduction: much more than previously thought," J. Assist Reprod. Genet. 31:627-636 (2014).
Fraccaroli et al., "A potential tolerogenic immune mechanism in a trophoblast cell line through the activation of chemokine-induced T cell death and regulatory T cell modulation," Human Reproduction, 24(1):166-175 (2009).
Gui et al., "Effects of Acupuncture on LIF and IL-12 in Rats of Implantation Failure," Am. J. Reprod. Immunol., 37:383-390 (2012).
Han et al., "Development of Luteinizing Hormone Releasing Hormone (LHRH) Delivery Systems for Vaginal Mucosal Route," Archives of Pharmaceutical Research, 18(5): 325-331 (1995).
International Search Report and the Written Opinion of the International Searching Authority corresponding to International Application No. PCT/GB2016/053080 (11 pages), dated Jan. 25, 2017.
Notification of Transmittal of the International Search Report and the Written Opinion of the International Searching Authority, or the Declaration corresponding to International Application No. PCT/GB2016/050175, dated Apr. 13, 2016.
Okada et al, "Vaginal Absorption of a Potent Luteinizing Hormone-Releasing Hormone Analog (Leuprolide) in Rats I; Absorption by Various Routes and Absorption Enhancement," Journal of Pharmaceutical Sciences, 71(12): 1367-1371 (1982).
Orsi et al. "Uterine and serum cytokine arrays in the mouse during estrus," Animal Reproduction Science, 100: 301-310 (2007).
Ostanin et al, "Role of Cytokines in the Regulation of Reproductive Function," Bulletin of Exp. Biology and Medicine, 143(1): 75-79 (2007).
Schjenken et al, "Seminal Fluid and Immune Adaptation for Pregnancy—Comparative Biology in Mammalian Species," Reprod. Dom. Anim., 49(3): 27-36 (2014).
Search Report corresponding to British Application No. GB1501302.2 dated Oct. 22, 2015.
Search Report under Section 17 corresponding to British Application No. GB1417607.7 (2 pages), dated Mar. 13, 2015.
Vujisic et al., "Ovarian follicular concentration of IL-12, IL-15, IL-18 and p40 subunit of IL-12 and IS-23," Human Reproduction, 21(1): 26-50-2655 (2006).
Zenclussen et al., "Questioning the Th1/Th2 Paradigm in Reproduction: Peripheral Levels of IL-12 are Down-Regulated in Miscarriage Patients," AJRI, 48: 245-251 (2002).
Search Report, GB Application No. 1 616 851.0, dated Jul. 24, 2017, 5 pages.

\* cited by examiner

EMBRYO IMPLANTATION

RELATED APPLICATIONS

This application claims priority to British Application No. GB 1314452.2, filed on Aug. 13, 2013 and U.S. Provisional Application No. 61/868,764, filed on Aug. 22, 2013. The contents of each of these applications are incorporated herein by reference in their entireties.

FIELD

The present invention relates to methods of and compositions for, improving the success rate of embryo implantation and the success rate of pregnancy in females, by providing an immunopermissive uterine environment prior to insemination or implantation of embryos. The methods of the present invention are used to make the uterus more receptive or less hostile to, for example, transferred embryos, sperm or other allografted tissue. The invention also includes inter alia compositions and formulations for use in the methods of the invention.

BACKGROUND

The uterine environment, which, if hostile/non-receptive, can be responsible for poor implantation rates of good quality embryos in human and animals alike. It is believed that an inadequately primed uterine environment may also be responsible for many cases of reproductive failure in terms of failed implantation and spontaneous abortion. Similarly, a failure in uterine priming is recognised in humans as being causative to pregnancy complications such as pre-eclampsia and foetal growth restriction by preventing appropriate placental development.

Genetically altered or modified animals provide valuable models for testing novel gene and drug therapies in vivo and are the main reason the numbers of animal experiments have been rising in the last decade. In the UK, over four times as many scientific procedures using genetically modified animals were carried out in 2011 as compared to 1995. The use of genetically modified animals now represents over 50% of all scientific procedures on animals. The largest category of use is breeding (to produce genetically modified animals), with rodents accounting for almost 1.8 million procedures in the UK in 2012 alone, on a background trend for this number to increase annually. Embryo transfer in rodents underpins the development of transgenic approaches, re-derivation of specific strains and facilitates the transport of animal-lines across large distances. Typically, embryo transfer requires induction of pseudopregnancy in recipient females. This phenomenon prepares the uterus for implanting embryos, however, the success rate of transferring genetically modified embryos, despite induction of pseudopregnancy, remains relatively low.

Mice are spontaneous ovulators and can become pseudopregnant following an estrus in which the female is mated with a genetically sterile male such as the T145H-Re strain (which is sterile due (which is sterile due to a chromosomal translocation) obtainable from Harlan Laboratories Inc, or a vasectomised male. Both sets of males ejaculate seminal plasma devoid of functional sperm. However, both genetically sterile and vasectomised mice are relatively costly. In the instance of vasectomised males, sterility cannot be guaranteed to be 100% effective and needs testing for each male, while the production of genetically sterile males generates unwanted surplus females.

Alternatively, pseudopregnancy can be induced by simulating the normal vaginal stimuli attained by mating with artificial mechanical stimulation, for example by a vibrating engraving tool (Kenney et al; *J Reprod. Fert.* 1977, 49, 305-309). It was found that the number and rate of intromissions were crucial influences on reproductive success (Diamond; *Science,* 1970, 169, 4, 995-997). Whilst this approach has seen some success in rats and mice mechanical stimulation had no effect on the induction of pseudopregnancy in the Golden Hamster (Diamond et al *J. Reprod. Fert.* 1968, 17, 165-168). When the female is mated with an infertile male or mechanically stimulated, the corpus luteum persists without an embryo, leading to pseudopregnancy. The female will develop mammary glands, lactate and build nests in the pseudopregnant state. There is a need to improve the methods of inducing a pseudopregnant state in laboratory test animals.

Although the protocols for embryo transfer in an array of rodent species are relatively well-established, their poor optimization means that there is a significant wastage of animals, raising a number of financial and ethical issues in animal units worldwide. The prior art standard approach currently relies on mating recipient females with vasectomised males to induce pseudopregnancy rather than mechanical stimulation, where copulatory activity and seminal exposure of the maternal reproductive tract triggers a neuroendocrine and localised (to the uterus, principally) inflammatory response involving a complex cascade of cytokine and prostaglandin-mediated events geared towards creating an immunopermissive environment in the uterus, thereby favouring pre-implantation embryo development and/or blastocyst implantation and the establishment of pregnancy. Even in the absence of fertilisation, luteal development and progesterone production are supported, and the maternal physiology is orchestrated to render the uterus receptive to transferred embryos for up to 10-13 days. This technique is routinely used to support the development of normal (cryopreserved strain regeneration/re-derivation) or genetically modified (transgenic/chimaeric/cloned) embryos.

However, the efficacy of this approach is limited. Typically, four times as many females are prepared for the procedure compared to those becoming pregnant. When implanting fresh or frozen embryos this represents a considerable wastage of valuable biological material and effort. Moreover, numbers of young vasectomised males also need to be maintained alongside the prospective recipients: these can only mate 2-3 times a week and are typically replaced every 6-9 months in order to maintain performance.

Mating predominantly occurs when the recipient female is in estrus. The estrus cycle lasts 4-5 days in the mouse and rat (equivalent to a woman's average 28 day menstrual cycle), which leads to the need to rely on a large pool of potential recipient females to take part in potential matings with vasectomised or otherwise sterile males. Typically, 75% of recipients are not in estrus in randomly cycling populations, leading to large numbers of females and vasectomised or otherwise sterile males being kept and, in the case of the former, often not used as surrogates in order to guarantee adequate numbers of recipients for use in timed transfers. This is particularly evident in instances where the embryos to be transferred are particularly valuable. Improvements to this approach have relied on timed estrus induction via the Whitten effect in recipient females. This strategy relies on pheremonal stimulation of recipient females, which typically brings them into estrus 3 days after exposure to stud male urine-soiled bedding. However, the cycling stage of females at the time of pheremonal exposure, proximity to stud cages and the age of recipients can all have adverse effects on the reliability of this approach, making it relatively ineffecient.

The chances of females being in estrus (sexually receptive) at the right time is 1:4 due to the length of their cycle (4 days). Thus, if 4 recipients are required, 16 females will be mated to 16 males, which translates to a 25% success rate. This figure can be even lower as some females will refuse to mate with their partner. The key point is that although most breeders either select females in estrus, or induce estrus before mating with sterile males, still only a relatively low percentage (often about 50%—but as low as 15% in some facilities) of oestrus females will become 'plugged' and so assumed to be pseudopregnant. Furthermore, females also have a very limited functional lifespan of a few months of age as embryo transfer recipients. Females rapidly accumulate abdominal fat as they mature, making laparotomic embryo transfers (the most common and successful method) technically too challenging.

By the compositions and methods of the present invention it is envisaged that the need for vasectomised or otherwise sterile male mice can be dramatically reduced along with a significant reduction of female mice usage.

The present invention aims to improve the pregnancy rates in mammalian females in terms of positive pregnancies and/or increased litter number following artificial or natural insemination or following transplantation of fresh or frozen or otherwise preserved embryos.

BRIEF SUMMARY OF THE DISCLOSURE

In accordance with the present inventions there is provided a composition of matter comprising any one, two, three or four cytokines selected from the group comprising TNF-α, TGFβ, Eotaxin and RANTES for use in improving pregnancy rates and/or for reducing maternal alloreactivity against seminal fluid/sperm or embryos or other allograft tissue and/or for providing an immunopermissive uterine environment in females prior to implantation of an embryo or prior to insemination.

The composition could therefore comprise TNF-α with one or more of TGFβ, Eotaxin and RANTES or TGFβ with one or more of Eotaxin and RANTES or Eotaxin and RANTES.

In some embodiments of the invention the composition may comprise a combination of any two, three or four of the cytokines selected from the group comprising TNF-α, TGFβ, Eotaxin and RANTES. It will be appreciated that the compositions of the present invention may therefore comprise a number of different combinations of 2 to 4 of the specified cytokines selected from the aforementioned list.

In some embodiments, the IL-12 is either IL-12 p40 or IL-12p70. In some embodiments, the MIP is either MIP-1a or MIP-1b.

In particular embodiments, the composition further comprises any one, two, three, four five or six additional cytokines selected from the group comprising IL-12, MCP-1, MIP, IL-17, IL-9, and GM-CSF. Thus, the composition of the present invention may be, as an illustrative example, TNF-α with one or more of TGFβ, Eotaxin and RANTES in addition to one or more of IL-12, MCP-1, MIP, IL-17, IL-9 and GM-CSF. It is within the scope of the invention to provide a number of specific combinations of the specified cytokines for use in inducing a uterus to be more receptive or less hostile to transferred embryo, sperm or other allografted tissue.

Accordingly the compositions of the present invention may include a variety of multiple cytokines as it is recognised that high concentrations of a specific cytokine in seminal fluid do not necessarily reflect their biological significance.

In some embodiments, the composition further includes any one or more of the additional cytokines selected from the group comprising IL-1α, IL-1p, IL-1ra, IL-2ra, IL-2, IL-3, IL-4, IL-5, IL-6, IL-7, IL-8, IL10, IL-13, IL-15, IL-16, IL-18, FGF, G-CSF, IFN-α2, IFN-γ, IP-10, PDGF, VEGF, CTACK, KC, GROα, HGF, ICAM-1, LIF, MCP-3, M-CSF, MIF, MIG, β-NGF, SCF, SCGF-β, SDF-1α, TNF-β, TRAIL and VCAM-1.

In some embodiments, the compositions of the present invention are selected from the following cytokines:
 (i) any one, two, three or four cytokines selected from the group comprising TNF-α, TGFβ, Eotaxin and RANTES; and optionally one or more additional cytokine selected from the group comprising;
 (ii) IL-12, MCP-1, MIP IL-17, IL-9, and GM-CSF and optionally a further additional cytokine selected from the group comprising;
 (iii) IL-1α, IL-1β, IL-1ra, IL-2ra, IL-2, IL-3, IL-4, IL-5, IL-6, IL-7, IL-8, IL10, 1L-13, IL-15, IL-16, IL-18, FGF, G-CSF, IFN-α2, IFN-γ, IP-10, PDGF, VEGF, CTACK, KC, GROα, HGF, ICAM-1, Leptin, LIF, MCP-3, M-CSF, MIF, MIG, β-NGF, SCF, SCGF-β, SDF-1a, TNF-β, TRAIL VGEF and VCAM-1.

It will be appreciated that the compositions of the present invention can comprise minimally 2 and up to 41 cytokines or any number there between.

Table 1 below lists the acronyms for cytokines referred to in embodiments of the present invention:

TABLE 1

| Cytokines analysed using bio-plex assays | |
|---|---|
| IL-1α | Interleukin-1α |
| IL-1β | Interleukin-1β |
| IL-1ra | Interleukin-1 receptor antagonist |
| IL-2ra | Interleukin-2 receptor antagonist |
| IL-2 | Interleukin-2 |
| IL-3 | Interleukin-3 |
| IL-4 | Interleukin-4 |
| IL-5 | Interleukin-5 |
| IL-6 | Interleukin-6 |
| IL-7 | Interleukin-7 |
| IL-8 | Interleukin-8 |
| IL-9 | Interleukin-9 |
| IL-10 | Interleukin-10 |
| IL12 (p40) | Interleukin-12 (p40) |
| IL-12 (p70) | Interleukin-12 (p70) |
| IL-13 | Interleukin-13 |
| IL-15 | Interleukin-15 |
| IL-16 | Interleukin-16 |
| IL-17 | Interleukin-17 |
| IL-18 | Interleukin-18 |
| Eotaxin | Eotaxin |
| FGF | Basic fibroblast growth factor |
| G-CSF | Granulocyte-colony stimulating factor |
| GM-CSF | Granulocyte macrophage-colony stimulating factor |
| IFN-α 2 | Interferon-α2 |
| IFN-γ | Interferon-γ |
| IP-10 | IFN-γ inducible protein-10 |
| LEPTIN | Hormone associated with weight control |
| MCP-1 | Macrophage chemotactic protein-1 |
| MIP-1α | Macrophage inflammatory protein-1α |
| MIP-1β | Macrophage inflammatory protein-1β |
| PDGF | Platelet derived growth factor |
| RANTES | Regulated upon activation normal T cell expressed and secreted |
| TNF-α | Tumour necrosis factor |

TABLE 1-continued

Cytokines analysed using bio-plex assays

| | |
|---|---|
| VEGF | Vascular endothelial growth factor |
| CTACK | Cutaneous T cell attracting chemokine |
| KC | Ketatinocyte derived cytokine |
| GROα | Growth regulated ongogene-α |
| HGF | Hepatocyte growth factor |
| ICAM 1 | Intercellular cell adhesion molecule |
| LIF | Leukaemia inhibitory factor |
| MCP3 | Monocyte chemoattractant protein-3 |
| M-CSF | Macrophage-colony stimulating factor |
| MIF | Macrophage migration inhibitory factor |
| MIG | Monokine induced by IFN-γ |
| β-NGF | Basic-nerve growth factor |
| SCF | Stem cell factor |
| SCGF-β | Stem cell growth factor-β |
| SDF-1α | Stromal cell derived factor-1α |
| TGF-β1 | Transforming growth factor β1 |
| TNF-β | Tumour necrosis factor-β |
| TRAIL | Tumour necrosis factor related apoptosis inducing ligand |
| VCAM-1 | Vascular cell adhesion molecule-1 |

The present invention resides in harnessing the properties of seminal agents which promote uterine receptivity and in providing a chemicophysical alternative to vasectomised or otherwise sterile males, preferably in the form of a vaginal insert such as a pessary, gel, spray or allied to any other dissolvable carrier.

The present invention, advantageously, given that the demand for transgenic non-human animal models is set to rise further, provides an alternative to vasectomised or otherwise sterile males inducing pseudopregnancy and also advantageously reduces the number of females required by improving uterine receptivity to transferred embryos.

The present invention advantageously obviates the need for vasectomised or otherwise sterile males given that their contribution solely relates to triggering the neuroendocrine and uterine inflammatory responses required to induce pseudopregnancy.

According to a further aspect of the invention there is provided a pharmaceutical composition as herein before described in the form of an intra-uterine device for improving pregnancy rates and/or for reducing maternal alloreactivity against seminal fluid/sperm or embryos or other allograft tissue and/or for providing an immunopermissive uterine environment in females prior to implantation of an embryo or prior to insemination.

In some embodiments, the female is mammalian and more preferably is human.

In some embodiments, the mammalian female is selected from the group comprising mouse, rat, rabbit, gerbil, guinea pig, hamster, primate (monkey, ape), canine, feline, porcine or any other laboratory animal or endangered species into which embryos are placed.

In particular embodiments, the female is a mammal and more preferably still is a rare breed/species or a breed/species that is endangered.

In some embodiments, the female may be selected from the group comprising animals in the orders of Artiodactyla, Carnivora, Cetacea, Chiroptera, Dermoptera, Edentata, Hyracoidae, Insectivora, Lagomorpha, Marsupialia, Perissodactyla, Pholidata, Pinnipedia, Primates, Proboscidea, Rodentia, Sirenia and Tubulidentata.

In some embodiments, the amount of any one of the cytokines present in the composition is released, from any one of its deliverable forms as described herein after, in situ either above or within their approximate physiological range found in seminal fluid.

Cytokines are measured as pg/ml as the standardised recognised values in the art.

The present invention resides in harnessing the properties of seminal agents, especially cytokines (which are protein modulators of the immune response and which promote uterine receptivity), by providing a chemicophysical formulation preferably in a form suitable for vaginal delivery for insertion into the female prior to mating/insemination or prior to implantation of embryos. The introduced formulation releases agents which enhance the receptivity of the uterine environment.

The approach used in the present invention is to mimic the biochemical signalling mediated by seminal plasma by using a pessary-based, gel-based, solution-based, emulsion-based, powder-based or aerosol-based delivery system. Pessaries are already routinely used in an array of large domestic species (e.g. cattle) for the synchronisation of estrous cyclicity for embryo transfer/artificial insemination. However, to date, no pessary has been used with the compositions of the present composition or for the specified function of promoting uterine receptivity and/or inducing a pseudopregnant state.

In some embodiments, the cytokines are recombinant. That is to say that they are made by genetically engineering a bacterium or other cell type using recombinant technology.

The present invention provides compositions for females comprising recombinant cytokine preparations, typically in the form of a pessary placed in the vagina or an aerosol foam released in the vagina prior to insemination/embryo transfer in order to reduce maternal immune alloreactivity against sperm/embryos, thereby improving pregnancy rate/outcome. The use of this mode of delivery as a strategy for improving endometrial receptivity is novel.

In some embodiments, the composition further includes adjuvants such as preservatives, anti-oxidants, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. It may also be beneficial to include waxes, water and co-solvents.

In some embodiments, the composition is in a form suitable for vaginal delivery such as a vaginal capsule, vaginal gel, vaginal tablet, vaginal powder, vaginal solution, vaginal pessary, vaginal cup, vaginal sponge or vaginal foam or spray. Most preferably the composition is in the form of a vaginal pessary.

In particular embodiments, the vaginal formulation is dissolving or non-dissolving, degradable or non-degradable.

In some embodiments, the compositions of the present invention are prepared as a vaginal suppository, tablet, powder, bioadhesive tablet, capsule, microparticle, bioadhesive microparticle, microcapsule, microsphere, liposome, cream, lotion, foam, spray, film, ointment, solution, gel, or a sustained release gel, tablet or capsule, or a sustained release suppository administered to the vagina or incorporated into a vaginal device.

In an alternative embodiment of the invention the compositions of the present invention are prepared for oral or rectal administration or as an enteric coated tablet for use in gastrointestinal tract delivery so that they may be absorbed from the mucosa of the gastrointestinal tract. The rationale for these modes of administration is that the mucosal immune system in the digestive system is linked to that of the reproductive tract. In this way, mucosal priming will occur, thereby facilitating embryo implantation, allograft/ gamete/embryo tolerance, self-immunotolerance or tolerance of the endogenous/exogenous microflora of both the reproductive and digestive tracts.

In some embodiments, the compositions of the present invention are prepared as multiwalled, multicored, microencapsulated preparations. More preferably, the active components of the composition are when used as dried material encapsulated in a shell/coat like a gelatin capsule.

Compositions for vaginal administration are preferably prepared by mixing the compositions of the present invention with suitable pharmaceutical ingredients or non-irritating excipients or carriers such as cocoa butter, polyethylene glycol or a suppository wax which are solid at room temperature but liquid at body temperature and therefore melt in the rectum or vaginal cavity and release the active compound. A typical example of a vaginal pessary would include the active ingredients and the following excipients: medium chain tryglycerides and hard fat.

Alternatively, the composition can be incorporated into an intravaginal device or a coating of such device, for example, a tampon or tampon-like device coating, or incorporated into a sponge, foam, strip, powder, pessary, or other material. Absorbent material or matrix of such devices may be impregnated with a composition of the present invention as a liquid solution, suspension lotion, powder, cream, microemulsions or suspension of liposomes, bioadhesive nanoparticles, or bioadhesive microparticles. In some embodiments, the vaginal device is dissolving or non-dissolving, degradable or non-degradable.

In some embodiments, the compositions further include a mucoadhesive agent, sorption promoter or penetration enhancer. The compositions of the present invention are delivered by transmucosal vaginal delivery and comprise contacting the vaginal mucosa with the compositions of the present invention.

In some embodiments, the compositions for vaginal delivery are for rapid delivery, controlled delivery, continuous delivery or pulsed delivery.

It is envisaged that the composition of the present invention will be formulated in one embodiment as a pessary with a slow wax melt or a fast wax melt to achieve continuous or rapid delivery respectively. In an alternative embodiment, the composition of the invention will be formulated into a foam or gel with appropriate additives to permit controlled release.

In some embodiments, in the instance of providing the composition of the present invention as a vaginal pessary, tablet, bioadhesive tablet, capsule, powder, microparticle, bioadhesive microparticle, that the coating will be abrasive. This is an appropriate modification to the deliverable composition, especially if the penis of the male of the species to be prepared for uterine receptivity has a rough epidermis, keratinous spines, etc. In this instance it is desirable for the inserted vaginal delivery vehicle to have a rough outer coating similar to that as on the penis in order to elicit a maternal inflammatory response to improve penetration of the preparation into the mucosa, elicit an initial inflammatory response and aid generic neuroendocrine stimulation.

In a particular embodiment of the invention, the composition is in the form of a pessary. Preferably the pessary is suitably sized and shaped so as to be inserted into the vagina of the female. The pessary may have a solid core and an outer porous layer. Typical dimensions of a pessary for mice are overall diameter of 4 mm and a length of 7 mm. The diameter and length of the pessary is dependent upon the size of the vagina of the species into which it is inserted, it is desirous that the pessary be sized and shaped so that when inserted into the vagina it is retained without discomfort.

According to a further aspect of the invention there is provided the composition of the first aspect of the invention for the manufacture of a medicament for improving pregnancy rates and/or reducing maternal alloreactivity against seminal fluid/sperm or embryos or other allograft tissue and/or for providing an immunopermissive uterine environment in females prior to implantation of an embryo or prior to insemination.

According to a further aspect of the invention there is provided a method of reducing maternal alloreactivity in a female against seminal fluid/sperm, embryos or other allograft (including existing microflora) comprising exposing the vaginal/gastrointestinal tract mucosa to a composition as hereinbefore described, the method comprising:
(i) introducing at least one vaginal delivery vehicle comprising the composition of the present invention into the vagina of the female;
(ii) optionally inserting further vaginal delivery vehicle (s);
(iii) allowing a sufficient period of time to elapse to allow the active components of the vaginal delivery vehicle to be released and to penetrate into the vagina and be absorbed transmucosally and/or diffuse and/or be transported into the uterus and/or through the gastrointestinal tract mucosa; and
(iv) inseminating the female by either mating with a male or by artificial insemination, donor gametes or introducing an embryo or other allograft into the uterus for implantation.

According to further aspect of the invention there is provided a method of improving pregnancy rate or outcome in a female prior to insemination or implantation of an embryo comprising exposing the vaginal/gastrointestinal tract mucosa to a composition as hereinbefore described, the method comprising:
(i) introducing at least one vaginal delivery vehicle comprising the compositions of the present invention into the vagina of the female;
(ii) optionally inserting further vaginal delivery vehicle (s);
(iii) allowing a sufficient period of time to elapse to allow the active components of the vaginal delivery vehicle to be released and to penetrate into the vagina and be absorbed transmucosally and/or diffuse and/or be transported into the uterus and/or through the gastrointestinal tract mucosa; and
(iv) inseminating the female by either mating with a male or by artificial insemination, donor gametes or introducing an embryo or other allograft into the uterus for implantation.

In a further embodiment of the invention, steps (iii) and (iv) are performed simultaneously/close chronological sequence in the case of artificial or natural insemination. The methods of the invention uses a composition comprising recombinant cytokine-containing pessaries, gel, spray or foam placed in the vagina at the time of insemination/embryo transfer to reduce maternal immune alloreactivity against sperm/embryos/gametes and endogenous or exogenous microflora, thereby improving pregnancy rate.

The number of doses and period between doses can be varied according to requirements and may vary depending on species or breed, super/ovulation status, seasonal effect, lactational status and number of previous failed pregnancies or previous inseminations or IVF treatments. It may also vary depending on maternal age and whether the female is primigravida.

In some embodiments, the methods of the invention when used for laboratory non-human animals further include the step of synchronizing estrus in recipient females.

According to a yet further aspect of the invention there is provided a kit of parts and optionally a set of written instructions therefore, the kit comprising a number of vaginal delivery vehicles containing the compositions of the invention and an apparatus for inserting said vaginal delivery vehicles into the vagina of the recipient female.

It will be appreciated that features described for the first aspect of the invention are equally applicable to each and all aspects of the invention and apply mutatis mutandis.

The invention will be described by way of example only with reference to the following figures wherein:

BRIEF DESCRIPTION OF THE DRAWINGS

Embodiments of the invention are further described hereinafter with reference to the accompanying drawings, in which.

DETAILED DESCRIPTION

Figure 1:
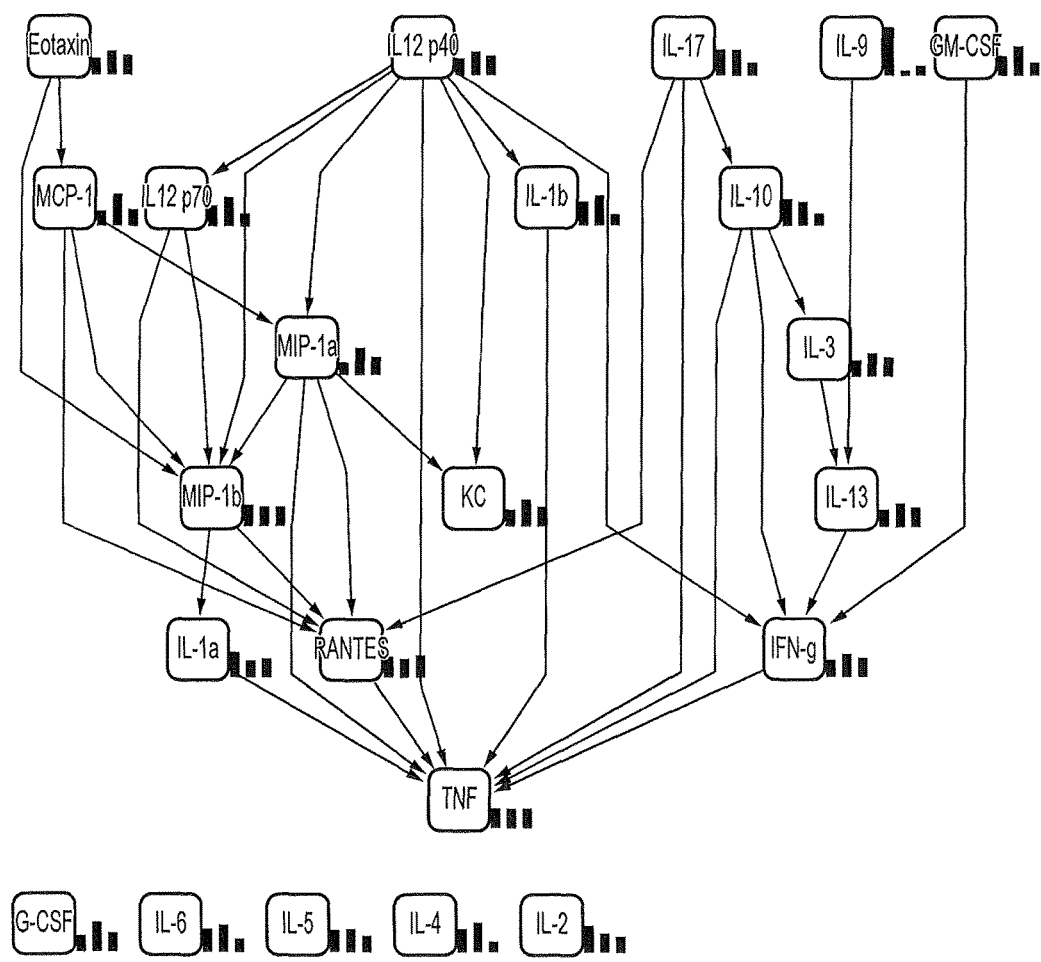
FIG. 1 shows the Bayesian mathematical modelling of cytokine networks in mouse seminal plasma. The nodes (cytokines) are colour-coded according to the conditional probability of corresponding mediator relative concentrations being high (green), low (red) or medium (white) concentration given the state(s) of their parent nodes (the bar charts adjacent to each node reflect underlying conditional probabilities of categorization into one of the three concentration bins from low on the left to high on the right). The normalized concentration (low or high) determines the intensity of the node colour. Edges (causal connecting lines between nodes) represent causal directed interactions between nodes. These cytokines will interact with the maternal reproductive tract to induce immunopermissiveness to paternal antigens.

Reference herein to "embryo" is intended to include a blastula, blastocyst, fertilized ovum or an organism in its early stages of development, especially before it has reached a distinctively recognizable form that is to be implanted into a female recipient. The terms are used interchangeably.

Reference herein to an "improved pregnancy rate" is intended to include a positive pregnancy outcome or improved perinatal survival or general viability following artificial insemination with processed semen or natural insemination or following transplantation of fresh or frozen or otherwise preserved embryos. The term pregnancy as used hereinafter is to be interpreted as encompassing a pregnancy resulting from natural or artificial insemination or following transplantation of a fresh or frozen or otherwise preserved embryo(s) and gametes.

Reference herein to an "intra-uterine device" is intended to include any pessary-based, gel-based, solution-based, emulsion-based, powder-based or aerosol-based delivery system that is capable of delivering the compositions of the present invention into the vagina so as to permit the compositions of the present invention to have a pharmacological effect on the uterine environment.

Reference herein to a "pessary" is intended as a means of delivery of the pharmaceutical substances of the present invention so that they are easily absorbed through the mucosal surfaces of the vagina, or intended to have action in the locality, for example against inflammation, or on the uterus.

"Pharmaceutical ingredient" or "excipient" means a pharmacologically inactive pharmaceutically acceptable compound added to a mucoadhesive composition of the invention. The ingredient or excipient does not have any pharmacological properties.

"Rapid delivery" means initial immediate rapid release and delivery of the components from the composition. The rapid delivery is typically followed by a time-dependent reduction in release of the components from the composition or device and delivery of the drug to the plasma/uterine wall tissues (or gastrointestinal tract, where appropriate).

"Controlled delivery" means a release wherein the active agent is released from the material in a predesigned manner. The release of the active agent may be constant over a long period, it may be cyclic over a long period, or it may be triggered by the environment or other external events.

"Continuous delivery" means continuous and uninterrupted release of the components from the formulation or device and delivering such components in a continuous manner. Continuous delivery may be preceded by the rapid delivery.

"Pulsed delivery" means a release and delivery of the components in intermittent intervals. Such pulsed delivery may be provided, for example, by formulating the composition in individual layers interspaced with inactive layers of dissolvable coatings or by using different pharmaceutical ingredients.

Seminal Fluid Cytokine Analysis

Sexually mature CD1 male mice (n=20) and Wistar rats (n=20) were sacrificed and seminal fluid collected from the seminal glands post mortem, a post mortem approach was chosen to avoid collecting samples by electroejaculation since semen quality is variable by this method, and because the samples coagulate rapidly, making analysis problematic. Seminal vesicle sampling is ideal as the fluid (rather than that of the accessory glands) contains the maternal tract immunomodulatory factors investigated and because coagulating gland secretions can more easily be avoided.

Seminal fluid samples were weighed individually, suspended in phosphate buffered saline (PBS) supplemented with 0.5% bovine serum albumin (BSA), and weighed again. By inference to standard weight:volume ratio of murine seminal fluid, it was possible to determine the original volume isolated and the dilution factor introduced by the PBS. This step was necessary because the fluid is too viscous to be pipetted accurately. Samples were spun and the supernatant frozen at −80° C. until analysed simultaneously for the following 23 cytokines: interleukin (IL)-1α, IL-1β, IL-2, IL-3, IL-4, IL-5, IL-6, IL-9, IL-10, IL-12 (p40), IL-12 (p70), IL-13, IL-17, eotaxin, granulocyte-colony stimulating factor (G-CSF), granulocyte macrophage-colony stimulating factor (GM-CSF), interferon (IFN)-γ, keratinocyte-derived chemokine (KC), monocytes chemotactic protein (MCP)-1, macrophage inhibitory protein (MIP)-1α, MIP-1β, regulated upon activation normal T cell expressed and secreted (RANTES) and tumour necrosis factor (TNF)-α.

This was achieved by custom 23-plex fluid-phase immunoassay kits run on a Luminex-100™ equipped with StarStation™ software. Serum diluent was used in all cases to avoid false positive/negatives and dilution adjusted to 1:1 in order to maximise sensitivity to baseline levels. Similar analysis was performed on rat seminal fluid.

Example 1

Table 2 below shows a variety of cytokines analyzed and measured in mouse seminal fluid. Eotaxin and RANTES appear to be the predominant cytokines present, with levels above 500 pg/ml. IL-9, TNF-α and MIP-1a had levels above 100 pg/ml whereas several cytokines such as G-CSF and IFN-γ had levels between 50-100 pg/ml and several others such as IL-13 and TGF-β had levels below 50 pg/ml.

TABLE 2

| Mouse | Mean | SEM |
|---|---|---|
| IL-1α | 8.19 | 1.96 |
| IL-1β | 87.48 | 9.04 |
| IL-2 | 3.03 | 0.49 |
| IL-3 | 0.35 | 0.04 |
| IL-4 | 0.11 | 0.01 |
| IL-5 | 0.56 | 0.07 |
| IL-6 | 3.63 | 0.44 |
| IL-9 | 135.14 | 33.47 |
| IL-10 | 19.95 | 3.36 |
| IL-12 p40 | 5.25 | 0.53 |
| IL-12 p70 | 10.91 | 1.08 |
| IL-13 | 20.64 | 1.86 |
| IL-17 | 5.10 | 0.90 |
| Eotaxin | 857.22 | 73.85 |
| G-CSF | 45.03 | 3.33 |
| GM-CSF | 4.16 | 0.39 |
| IFN-γ | 46.38 | 3.95 |
| KC | 37.17 | 3.56 |
| MCP-1 | 30.23 | 2.65 |
| MIP-1α | 114.32 | 8.31 |
| MIP-1β | 6.68 | 1.36 |
| RANTES | 618.62 | 84.17 |
| TNF-α | 102.27 | 9.11 |
| TGF-β | 27.63 | 6.54 |

Table 3 below shows a variety of cytokines analyzed and measured in rat seminal fluid. RANTES appears to be the predominant cytokine present. Of the cytokines analyzed only RANTES and GRO/KC had levels above 200 pg/ml. IL-10 and IL-6 had levels above 100 pg/ml, whereas several cytokines such as MCP-1 had levels between 50-100 pg/ml and several others such as IL-17 had levels below 50 pg/ml.

TABLE 3

| Rat | Mean | SEM |
|---|---|---|
| IL-1α | 3.28 | 0.97 |
| IL-1β | 20.41 | 0.84 |
| IL-2 | 29.11 | 3.40 |
| IL-4 | 20.17 | 1.13 |
| IL-5 | 9.58 | 0.95 |
| IL-6 | 149.17 | 1.13 |
| IL-9 | 54.56 | 0.84 |
| IL-10 | 114.89 | 1.45 |
| IL-12 p70 | 55.14 | 4.31 |
| IL-13 | 8.29 | 1.35 |
| IL-17 | 15.80 | 1.11 |
| IL-18 | 6.66 | 0.89 |
| TNF-α | 2.27 | 0.16 |
| IFN-γ | 2.93 | 0.39 |
| Eotaxin | 34.84 | 1.45 |
| GCSF | 1.51 | 0.07 |
| GMCSF | 40.53 | 2.10 |

TABLE 3-continued

| Rat | Mean | SEM |
|---|---|---|
| MCP-1 | 61.56 | 2.21 |
| LEPTIN | 43.69 | 2.61 |
| MIP-1α | 0.13 | 0.02 |
| IP-10 | 4.24 | 0.34 |
| GRO/KC | 228.00 | 2.10 |
| RANTES | 287.31 | 2.21 |
| VEGF | 0.00 | 0.00 |
| TGF-β | 0.00 | 0.00 |

Example 2

Eotaxin and RANTES appear to be the predominant cytokines each being present in an amount of more than 500 pg/ml (see Tables 1 and 2). The cytokines IL-1α, IL-6, IL-10, IL-12 (p40), IL-12 (p70), GM-CSF and MIP-1β were present at levels below 20 pg/ml and cytokines IL-1β, IL-9, 1L-13, G-CSF, TNF-α, MCP-1, KC, MIP-1α and IFN-γ were present at levels above 20 and below 150 pg/ml.

Based on these analyses, a solution of cell culture-tested recombinant mouse cytokines was made up in PBS using recombinant cytokines at the concentrations found in seminal fluid (Table 3). This was stored at −80° C. until required for imbibing the pessary.

TABLE 4

Cytokine Concentrations in utero in a Mouse
Pessary Preparation once solubilised.

| Cytokine | Pessary solution concentration (pg/ml) |
|---|---|
| IL-1α | 8.19 |
| IL-1β | 87.48 |
| IL-6 | 3.63 |
| IL-9 | 135.14 |
| IL-10 | 19.95 |
| IL-12 (p40) | 5.25 |
| IL-12 (p70) | 10.91 |
| IL-13 | 20.64 |
| G-CSF | 45.03 |
| GM-CSF | 4.16 |
| TNF-α | 102.27 |
| MCP-1 | 30.23 |
| RANTES | 618.62 |
| Eotaxin | 857.22 |
| KC | 37.17 |
| MIP-1α | 114.32 |
| MIP-1β | 6.68 |
| IFN-γ | 46.38 |

Pessaries also include an amount of TGF-β1 as this is important in eliciting uterine receptivity.

Example 3

Additional formulation components of pessaries for laboratory animals was dictated principally by toxicity (in case of accidental ingestion), palatability (to dissuade ingestion) and impact on luminal pH (the bioactivity of certain cytokines is promoted by vaginal pH). The size and shape of the pessaries is largely determined by the species for which their use is intended. For example, pessaries of approximately 4 mm in diameter are particularly suitable for mice since the size has been determined as appropriate for insertion without undue discomfort and is also of a suitable size to be retained in the vaginal vestibule. Larger laboratory animals or indeed larger breeds of mice may necessitate larger pessaries.

Pessaries were made from laser-etched nylon at a setting of between 5-10 Watts, use of this technique makes it possible to manipulate porosity (which facilitates 'loading') and overall shape and dimensions. It is envisaged that pessaries will be provided in a range of sizes and that the stalks may be snapped off from a central holding unit for use as desired and that a range of different sizes of pessaries may be provided to the user. Pessaries are prepared for use by soaking them overnight in 500 µl of 100 times the concentration of cytokine solution so as to load the pessaries with the necessary active agents to guarantee a seminal fluid like final concentration in the maternal reproductive tract. A pessary head is then removed from the stalk and inserted by means a suitable device directly into the mouse vagina. The pessary is then left in the mouse vagina for a period of time and then it is either removed at the time of embryo transfer when the animals are anaesthetised, or it self-dissolves or the pessary self ejects once the active ingredients have been absorbed.

It will be appreciated that the above embodiment is only one example of a means of delivering the compositions of the present invention and that the pessary may be in the form of a slow or fast melt wax type formulation and that the method of delivering the compositions of the present invention may vary from species to species. The delivery means may also be in the form of a biodegradable product and for example, in humans a vaginal sponge may be a more convenient method of delivering the compositions.

Example 4

A full mix and three different combinations of reduced cytokine mixes, at physiological concentrations, were prepared as shown in the Table 5. The full mix comprised IL-12 (P40), RANTES, Eotaxin, MIP-1β, TNF-α, 1L13, IFN-γ, TGF-β, IL-1β, IL-6, 1L-12 (p70), MCP-1, IL-10, IL-1α, IL-9, GM-CSF, KC, MIP-1 and GCSF.

Figure 2:
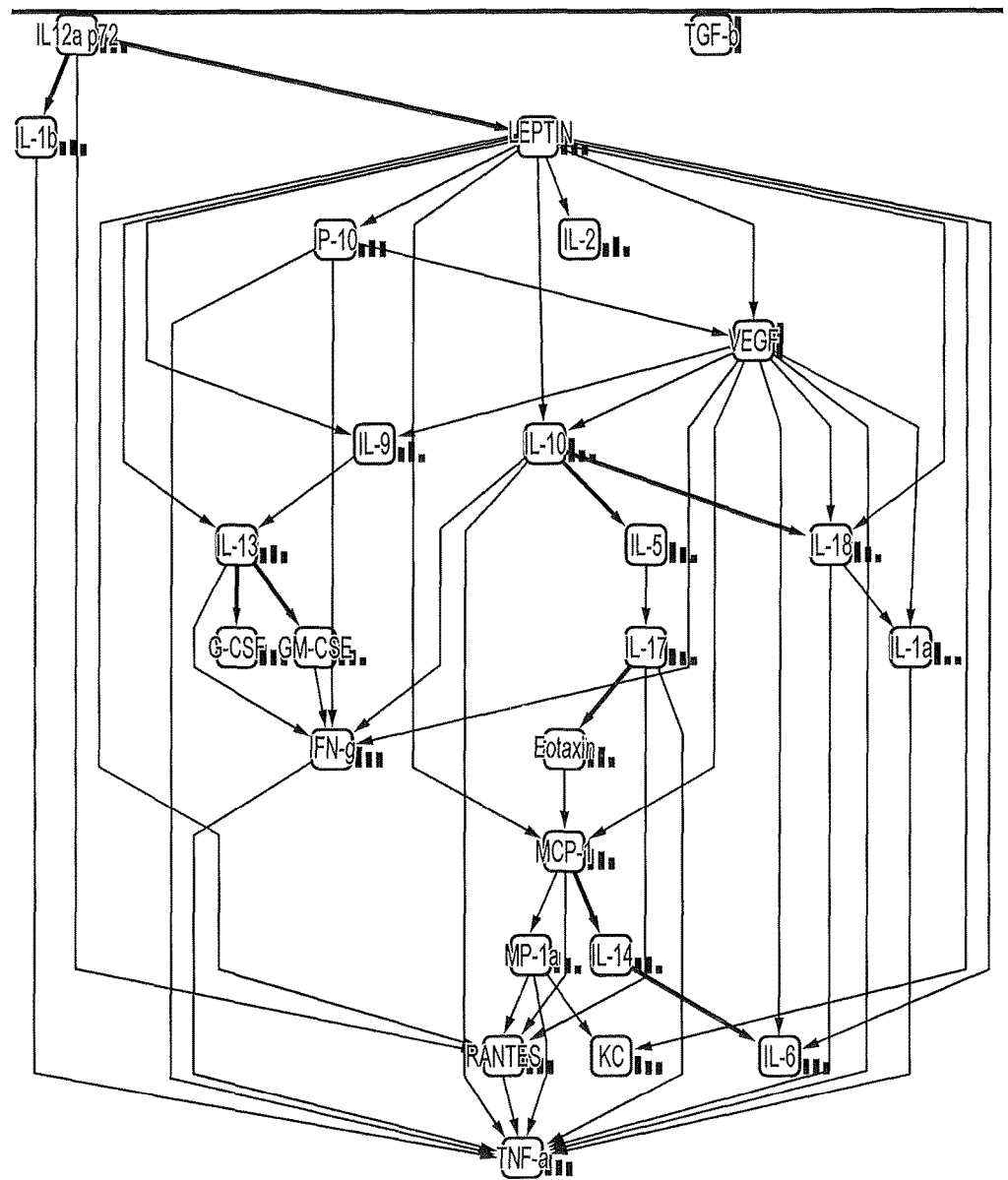
FIG. 2 shows the Bayesian mathematical modelling of cytokine networks in rat seminal plasma (details discussed above). Very high confidence level edges are coloured in red, based upon the confidence analysis of the Bayesian result (based on occurrence in >90% bootstrapping iterations).

Mix 1 contained IL-12 (P40), RANTES, MIP-1β, IL-13 and TGF-β. IL-12 (P40) was included due to its role as a major network ancestral parent (given the marked number of outgoing edges) and its putative causal control of multiple downstream mediators. RANTES and MIP-1β were included as these were hub nodes (likely involved in multiple signalling integration based on the high number of incoming edges). The importance of MIP-1 signalling highlighted by the conservation of this hub node function across species where its function is likely analogous to that highlighted in the rat network (FIG. 2) IL-13 was included following a similar rationale and because it appeared the be the principal node fulfilling this function in the right hand side of the network main branch illustrated in FIG. 1. TGF-β was included due to its purported potent immunomodulatory properties which temper the mating-induced inflammatory response.

Mix 2 contained IL-12 (P40), RANTES, MIP-1β, IL-13 and IFN-γ. The choice of mediators for this mix is given above with the exception of IFN-γ which, despite being a recognised abortifacient likely has a physiological role to play as a hub node at low levels as presented herein.

Mix 3 contained RANTES, TNF-α and TGF-β for the reasons highlighted above—TNF-α was added given that it was the only terminal node of the network. Its likely key role is underscored by the fact that its terminal node position was consistent across both the mouse and rat, despite the difference in species and the change in some of the network nodes analysed. Its role in reproductive immunity is hotly debated but it is increasingly being recognised as a likely key player in triggering the early inflammatory response associated with this process. This selection was based on the mathematical modelling of cytokine networks in seminal plasma (see FIGS. 1 and 2). The full mix composition is based on the most extensive murine multiplex immunoassay-based analysis available for seminal plasma analysis.

TABLE 5

The cytokine composition of the four pessaries used in this study (the checked boxes indicate inclusion in the mix)

| Cytokine | Full Mix | Mix 1 | Mix 2 | Mix 3 |
|---|---|---|---|---|
| IL-12 (p40) | ✓ | ✓ | ✓ | |
| RANTES | ✓ | ✓ | | ✓ |
| Eotaxin | ✓ | | ✓ | ✓ |
| MIP-1β | ✓ | ✓ | | |
| TNF-α | ✓ | | ✓ | ✓ |
| IL-13 | ✓ | ✓ | | |
| IFN-γ | ✓ | | ✓ | |
| TGF-β | ✓ | ✓ | | ✓ |
| IL-1β | ✓ | | | |
| IL-6 | ✓ | | | |
| IL-12 (p70) | ✓ | | | |
| MCP-1 | ✓ | | | |
| IL-10 | ✓ | | | |
| IL-1α | ✓ | | | |
| IL-9 | ✓ | | | |
| GM-CSF | ✓ | | | |
| KC | ✓ | | | |
| MIP-1α | ✓ | | | |
| G-CSF | ✓ | | | |

Figure 3:
FIG. 3 shows a bar chart of the percentage of successful deliveries following induction of pseudopregnancy by mating with a vasectomised male or a pessary (n=14 per group) of full mix, mix 1, mix 2 and mix 3.

The data shown in FIG. 3, confirms that the current nylon prototype pessary, 'loaded' with either a full complement or reduced numbers of cytokines, can successfully induce pseudopregnancy in CaCBAxC57Bl/6 F1 mice. We found that our three mixes of reduced cytokines gave different rates of success but that one combination in particular, Mix 3, induced pseudopregnancy with a similar success rate as purchased vasectomised males (n=14).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

That which is claimed is:

1. A composition consisting essentially of a recombinant eotaxin and a recombinant RANTES, wherein the composition releases the recombinant eotaxin and the recombinant RANTES in situ in a vagina within a physiological concentration range as corresponding eotaxin and RANTES found in seminal fluid of a fertile male.

2. The composition of claim 1, wherein the composition is shaped in the form of a vaginal insert or vaginal delivery system.

3. The vaginal insert or vaginal delivery system according to claim 2, wherein the recombinant eotaxin and the recombinant RANTES are active ingredients and are released in situ within the physiological concentration range as corresponding eotaxin and RANTES found in seminal fluid of the fertile male.

4. The vaginal insert or vaginal delivery system according to claim 2, wherein the vaginal insert or vaginal delivery system is a vaginal capsule, vaginal gel, vaginal tablet, vaginal powder, vaginal solution, vaginal pessary, vaginal cup, vaginal sponge, vaginal aerosol, vaginal foam or vaginal spray.

5. The vaginal insert or vaginal delivery system according to claim 2, further including an adjuvant, excipient or carrier.

6. A rodent pessary for transmucosal vaginal delivery comprising the composition according to claim 1.

7. The rodent pessary according to claim 6 for promoting uterine receptivity in a rodent.

8. The rodent pessary according to claim 6, wherein the rodent is a mouse or a rat.

9. A kit comprising:
   (i) a vaginal delivery vehicle comprising the composition of claim 1; and
   (ii) an apparatus for inserting said vaginal delivery vehicle into the vagina of a recipient female.

10. The composition of claim 1, wherein the recombinant eotaxin and the recombinant RANTES are the active ingredients.

11. A composition consisting essentially of a recombinant eotaxin, a recombinant RANTES, and one or more recombinant cytokines selected from the group consisting of TNF-α, TGF-β, IL-12, MCP-1, MIP, IL-17, IL-9, GM-CSF and combinations thereof, wherein the composition releases the recombinant eotaxin, the recombinant RANTES, and the one or more recombinant cytokines in situ in a vagina within a physiological concentration range as corresponding eotaxin, RANTES, and cytokines selected from the group consisting of TNF-α, TGF-β, IL-12, MCP-1, MIP, IL-17, IL-9 and GM-CSF found in seminal fluid of a fertile male.

12. The composition according to claim 11, wherein the IL-12 is IL-12 (p40) or IL-12(p70).

13. The composition according to claim 11, wherein the MIP is MIP-1a or MIP-1 b.

14. A method of reducing maternal alloreactivity against seminal fluid, sperm, or an embryo, the method comprising:
   (i) exposing a vaginal mucosa to a composition consisting essentially of a recombinant eotaxin and a recombinant RANTES, wherein the composition releases the recombinant eotaxin and the recombinant RANTES in situ in a vagina within a physiological concentration range as corresponding eotaxin and RANTES found in seminal fluid of a fertile male;
   (ii) introducing at least one vaginal delivery vehicle comprising the composition consisting essentially of the recombinant eotaxin and the recombinant RANTES into the vagina of a female, wherein the recombinant eotaxin and the recombinant RANTES are active ingredients;
   (iii) allowing a sufficient period of time to elapse to allow the active ingredients of the vaginal delivery vehicle to be released and to penetrate into the vagina and be absorbed into a uterus; and
   (iv) inseminating the female by either mating with a male or by artificial insemination, donor gametes or introducing an embryo into the uterus for implantation.

15. The method according to claim 14, wherein steps (iii) and (iv) are performed simultaneously or in close chronological sequence.

16. A method of improving pregnancy rate or outcome in a female prior to insemination or implantation of an embryo, the method comprising:
   (i) exposing a vaginal mucosa to a composition consisting essentially of a recombinant eotaxin and a recombinant RANTES, wherein the composition releases the recombinant eotaxin and the recombinant RANTES in situ in a vagina within a physiological concentration range as corresponding eotaxin and RANTES found in seminal fluid of a fertile male;
   (ii) introducing at least one vaginal delivery vehicle comprising the composition consisting essentially of the recombinant eotaxin and the recombinant RANTES into the vagina of the female, wherein the recombinant eotaxin and the recombinant RANTES are active ingredients;
   (iii) allowing a sufficient period of time to elapse to allow the active ingredients of the vaginal delivery vehicle to be released and to penetrate into the vagina and be absorbed into a uterus; and
   (iv) inseminating the female by either mating with a male or by artificial insemination, donor gametes or introducing an embryo into the uterus for implantation.

17. The method according to claim 16, wherein steps (iii) and (iv) are performed simultaneously or in close chronological sequence.

* * * * *